(12) United States Patent
Mehler et al.

(10) Patent No.: US 7,235,681 B2
(45) Date of Patent: Jun. 26, 2007

(54) METHOD FOR PRODUCING ORGANOALUMINUM COMPLEXES AND THE USE THEREOF FOR PRODUCING ELECTROLYTE SOLUTIONS FOR THE ELECTROCHEMICAL DEPOSITION OF ALUMINUM-MAGNESIUM ALLOYS

(75) Inventors: Klaus-Dieter Mehler, Mülheim/Ruhr (DE); Richard Lisowsky, Kamen (DE)

(73) Assignee: Aluminal Oberflachentechnik GmbH & Co. KG, Staudt (DE)

( * ) Notice: Subject to any disclaimer, the term of this patent is extended or adjusted under 35 U.S.C. 154(b) by 0 days.

(21) Appl. No.: 10/514,041

(22) PCT Filed: May 13, 2003

(86) PCT No.: PCT/EP03/04972

§ 371 (c)(1),
(2), (4) Date: Jul. 5, 2005

(87) PCT Pub. No.: WO03/102276

PCT Pub. Date: Dec. 11, 2003

(65) Prior Publication Data

US 2005/0272947 A1    Dec. 8, 2005

(30) Foreign Application Priority Data

May 31, 2002 (DE) ............................ 102 24 089

(51) Int. Cl.
*C07F 5/06* (2006.01)
*C25D 3/00* (2006.01)

(52) U.S. Cl. ............... 556/187; 205/236; 205/237; 106/1.25

(58) Field of Classification Search ............. 556/187; 205/236, 237; 106/1.25
See application file for complete search history.

(56) References Cited

U.S. PATENT DOCUMENTS

| | | | | |
|---|---|---|---|---|
| 3,361,781 | A | * | 1/1968 | Ziegler et al. .............. 556/187 |
| 3,691,221 | A | * | 9/1972 | Kobetz et al. .............. 556/102 |
| 4,900,854 | A | * | 2/1990 | Winterton et al. ........... 556/70 |
| 5,834,058 | A | | 11/1998 | Wallbridge et al. |
| 6,734,317 | B2 | * | 5/2004 | Heitmann et al. .......... 556/187 |

FOREIGN PATENT DOCUMENTS

| | | |
|---|---|---|
| CA | 2352800 A1 * | 6/2000 |
| DE | 1 056 377 | 4/1959 |
| DE | 0 084 816 | 8/1983 |
| WO | WO 00/32847 | 6/2000 |

* cited by examiner

Primary Examiner—Porfirio Nazario-Gonzalez
(74) Attorney, Agent, or Firm—Knobbe, Martens Olson & Bear LLP

(57) ABSTRACT

The invention relates to a method for producing electrolyte solutions consisting of trialkylaluminium $AlR_3$, $M^1AlR_4$, $M^2AlR_4$ and an aromatic hydrocarbon. According to the invention, a mixture of $M^1OR$ and $M^2OR$ is reacted with trialkylaluminium $AlR_3$ at temperatures below 25° C. in an aromatic hydrocarbon. $M^1AlR_4/M^2AlR_4$ is isolated from the obtained mixture and a ready-for-use electrolyte for the electrochemical deposition of aluminum-magnesium alloys is obtained by the addition of aromatic hydrocarbon.

6 Claims, No Drawings

METHOD FOR PRODUCING ORGANOALUMINUM COMPLEXES AND THE USE THEREOF FOR PRODUCING ELECTROLYTE SOLUTIONS FOR THE ELECTROCHEMICAL DEPOSITION OF ALUMINUM-MAGNESIUM ALLOYS

RELATED APPLICATIONS

This application is a US National Phase of International Patent Application No.: PCT/EP03/04972 filed on May 13, 2003, designating the USA and published in German on Dec. 11, 2003 as WO 03/102276, which claims the benefit of German Patent Application No.: 102 24 089.2, filed May 31, 2002.

FIELD OF THE INVENTION

The invention relates to an improved method for the production of organoaluminum complexes, which complexes are used in the production of electrolyte solutions for the electrolytic deposition of aluminum-magnesium alloys.

BACKGROUND OF THE INVENTION

Organoaluminum complexes have been used in the electrolytic deposition of aluminum for quite some time (Ph.D. Thesis by H. Lehmkuhl, T H Aachen 1954, DE-PS 10 47 450, K. Ziegler, H. Lehmkuhl, Z. Anorg. Allg. Chemie 283, 414 (1956); DE-PS 10 56 377; H. Lehmkuhl, Chem. 1 ng. Tech. 36, 616 (1964); EP-A-0 084 816; H. Lehmkuhl, K. Mehler and U. Landau in Adv. in Electrochem. Science and Engineering (Ed. H. Gerischer, C. W. Tobias) Vol. 3, Weinheim 1994).

There has been rapidly increasing interest in electrolytic coating of metallic materials with aluminum or aluminum-magnesium because such coatings have excellent corrosion protection and are ecologically safe. Therefore, electroplating using organoaluminum electrolytes operating at moderately elevated temperatures of between 60 and 150° C. and in closed systems is of major technical importance.

The PCT/EP application WO 00/32847 describes organoaluminum electrolytes suitable for electrochemical deposition of aluminum-magnesium alloys in technical applications as well. Such electrolytes contain alkali tetraalkylaluminum components, particularly K[AlEt$_4$], and in a preferred embodiment in mixture with Na[AlEt$_4$], the molar ratio of sodium/potassium component being less than 1:3. These electrolytes also contain trialkylaluminum, preferably AlEt$_3$, as well as toluene or liquid xylene as preferred solvent.

RELATED ART

Methods known from the literature (Houben-Weyl, XIII/4 (1970), pp. 110–120; L. I. Zakharkin and V. V. Gavrilenko, Ž. obšč. Chim. 32, 689 (1962); engl.; 688; H. Lehmkuhl, K. Ziegler in Houben-Weyl, XIII/4 (1970), p. 120; E. B. Baker and H. H. Sisler, Am. Soc. 75, 5193 (1953)) and used for the production of such organoaluminum complex compounds are complicated, involving crucial disadvantages. Thus, the complexes MAlR$_4$ (M=Na, K, Rb, Cs, R=alkyl residues having preferably one, two or four C atoms) require costly separate production and isolation before being reacted in further reaction steps, using aluminum alkyls AlR$_3$ and aromatic hydrocarbons, to form the corresponding mixtures which furnish usable electrolyte solutions after work-up.

Well-known methods of producing such electrolytes not only have the disadvantage of involving several steps, including the necessity of isolating the corresponding pyrophoric intermediates, but also, the yields are reduced. Waste products and solvents, the handling of which involves high input and cost, must be disposed of.

To date, the electrolyte solutions (e.g. 0.8 mol of K[AlEt$_4$]/0.2 mol of Na[AlEt$_4$]/2.0 mol of AlEt$_3$/3.3 mol of toluene) identified as particularly effective in WO 00/32847 can only be produced via separate production of Na[AlEt$_4$] and K[AlEt$_4$], isolating and mixing the latter at the proper K/Na ratio, and subsequent addition of toluene and trialkylaluminum, with all the disadvantages mentioned above.

Thus, for example, WO 00/32847 uses NaAlR$_4$ which has to be produced separately at first. Said NaAlR$_4$ can be produced as follows: sodium hydride and aluminum triethyl are combined to form the complex Na[HAlEt$_3$] in a solvent which has to be removed and disposed of, the formation of the sodium hydride complex melting at 64° C. proceeding smoothly in an exothermic reaction. This is followed by the technically complex pressurized reaction of the pyrophoric compound with ethene gas to be introduced to form the Na[AlEt$_4$] complex, the rate of ethene addition depending on four factors: stirring, temperature, pressure, and amount of excess NaH in the complex. Thus, the reaction proceeds very slowly at 145–155° C., while from 180° C. on, the rate of addition must be slowed down by cooling the reactor, and from 190° C. on, there is a risk of uncontrolled reaction due to overheating, merely resulting in impure, brown products. Also, markedly increased values of butyl groups are noted at elevated temperatures as a result of build-up reactions. In total, production in a batch process on the above route is difficult to control. Following isolation of Na[AlEt$_4$], again leaving solvent, reaction with KCl with partial exchange of Na for K is effected, resulting in an equilibrium ratio of Na/K of 1:4 and necessitating filtration and disposal of the NaCl having formed, followed by addition of triethylaluminum and toluene to adjust the final concentration of the electrolyte.

Due to the equilibrium concentration, the above method merely allows production of electrolyte solutions with a ratio of Na/K=approx. 0.2:0.8 and therefore cannot be used universally. Adjusting other mixing ratios therefore requires separate production and isolation of K[AlEt$_4$] as well (e.g. in a process similar to that specified for Na[AlEt$_4$], using potassium hydride in a high-boiling aliphatic hydrocarbon), whereafter the K/Na ratio to be adjusted is achieved by mixing K[AlEt$_4$] and Na[AlEt$_4$] and the usable electrolyte solution is obtained by subsequent addition of further components. Another problem in the above procedure is lacking industrial availability of the sodium hydride starting component. Once produced, the system is employed in an electroplating process, thus preventing the use of industrial sodium hydride suspensions in white oil.

With industrially available alkali alkanolate, the production of alkali aluminum tetraalkyl from alkanolate appears to be much easier (DAS 1153754 (1958), K. Ziegler, inventors: K. Ziegler and H. Lehmkuhl; CA 60, 1794 (1964); H. Lehmkuhl, K. Ziegler in Houben-Weyl, XIII/4 (1970), p. 116; H. Lehmkuhl and R. Schäfer, A. 705, 32 (1967); H. Lehmkuhl, Ang. Ch. 75,1090 (1963)).

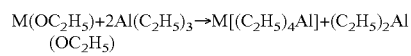

M=K, Na

However, the literature (H. Lehmkuhl, K. Ziegler in Houben-Weyl XIII/4 (1970), p. 116) makes reference to the fact that a particular methodology must always be maintained, considerably impeding industrial production. Quotation:

"In reactions of alkali alkanolates with trialkylaluminum, care must be taken that excess alkali alkanolate never be present in the mixture—not even temporarily. Otherwise, the respective test batch will immediately turn brown. Presumably, the explanation is that the alkanolate, in accordance with the above-specified order of complex formation tendency, liberates the alkylmetal compound whose further, as-yet unknown reactions cause the brown discoloration. Therefore, always add a well-stirred suspension of dry alcoholate in a hydrocarbon to the alkylaluminum compound."

Due to the insolubility of the alkali alkanolate in hydrocarbons or aromatic hydrocarbons, the process step of continuously adding the insoluble component in the form of a suspension can only be accomplished with high input in a technical production. For this reason, the more or less massively occurring brown discoloration as a result of undesirable reaction byproducts (possibly from reactions with the aromatic solvent) has been tolerated in previous test batches. However, electrolytes produced in this fashion merely result in systems of limited lifetime or in non-utilizable coatings.

Consequently, for technical applications of the electrolytes described above, there is a demand in a process for the low-cost production of substantial amounts of alkali aluminum tetraalkyl including no byproduct impurities.

SUMMARY OF THE INVENTION

Surprisingly, and in contrast to the above-cited literature, it was found that alkali aluminum tetraalkyl in the desired form can also be produced by continuous addition of the trialkylaluminum to previously supplied alkali alkanolate, provided heating of the reaction mixture above 25° C. is avoided by means of suitable measures (e.g. cooling).

Thus, a method for the production of organoaluminum complex compounds of general formula $MAlR_4$ is provided, wherein M=Li, Na, K, Rb, Cs, $NR_4^+$, and R is an alkyl residue with a maximum of 4 C atoms, in which method an alkanolate of general formula M(OR) or mixtures of several alkanolates, e.g. of two alkanolates $M^1(OR)$ and $M^2(OR)$ ($M^1 \neq M^2$), in aromatic solvents are supplied and reacted with at least one trialkylaluminum compound of general formula $AlR_3$, and the organoaluminum complex compounds are subsequently isolated from the reaction mixture according to per se known methods, characterized in that the reaction is performed at temperatures of 25° C. at maximum, preferably 20° C. at maximum.

In this way, absolutely colorless final products can be obtained.

Compounds produced according to this method can be employed in the production of electrolyte solutions in accordance with WO 00/32847 for the electrolytic deposition of aluminum-magnesium alloys on electroconductive materials, using soluble aluminum and magnesium anodes or anodes made of aluminum-magnesium alloy.

DETAILED DESCRIPTION OF THE PREFERRED EMBODIMENT

Production of a Ready-for-Use Electrolyte Solution:

Step 1: The Educts are Reacted According to the Following General Reaction Equation

$4\ AlR_3+M^1OR+M^2OR+\text{arom. HC} \rightarrow M^1AlR_4+M^2AlR_4+2R_2AlOR+\text{arom. HC HC}$ in an aromatic hydrocarbon at temperatures of −20 to 25° C., preferably 0 to 20° C., under inert gas atmosphere. Thereafter, the aromatic hydrocarbon is distilled off to be re-used in step 2, followed by distillation of $R_2AlOR$ which can be obtained in pure form (and represents an important raw material—especially where R=ethyl—which can be utilized commercially, thereby contributing to the economy of this method and to avoiding waste). In this way, the mixture $M^1AlR_4/M^2AlR_4$ is obtained.

However, alternative separation procedures for the mixture $M^1AlR_4/M^2AlR_4$ are also possible. Thus, for example, the $M^1AlR_4/M^2AlR_4$ can be precipitated by allowing the reaction solution to stand at room temperature—accelerated by lower temperatures—and obtained in pure form, using methods such as phase separation, filtration or decanting, and separated from the solvent and from the $R_2AlOR$ dissolved therein.

Step 2

The resulting mixture $M^1AlR_4/M^2AlR_4$ is mixed with $AlR_3$ and aromatic hydrocarbon such as benzene, toluene, xylene to form the ready-for-use electrolyte solution:

The method allows any selection of the molar ratios of $M^1OR/M^2OR$ in the first step and addition of any amount of $AlR_3$ and aromatic hydrocarbon in the second step, so that the new method permits adjusting any desired ratio of $AlR_3/(M^1AlR_4+M^2AlR_4)/$aromatic hydrocarbon and can therefore be used in a general fashion in the production of appropriate electrolyte solutions.

When optimally implemented, no waste will be formed, and handling of pyrophoric starting materials and intermediate compounds, which do not require isolation and are obtained in quantitative yield, is reduced to a minimum, thereby substantially contributing to the safety and economy of the method.

Furthermore, the economy is increased by the commercial usability of the $Et_2AlOEt$ formed in step 1 when using $AlEt_3$, the former representing another important useful raw material.

EXAMPLE

Production of an Electrolyte for Aluminum-Magnesium Coating:

Desired Electrolyte Composition:

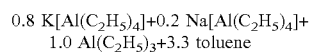

$0.8\ K[Al(C_2H_5)_4]+0.2\ Na[Al(C_2H_5)_4]+1.0\ Al(C_2H_5)_3+3.3\ \text{toluene}$ 1. Reacting the mixed alcoholate with $Al(C_2H_5)_3$ ("TEA")
2. Removing the $Et_2AlOEt$ by-component
3. Adjusting the final mixture with TEA and toluene
4. Checking the behavior relating to conditioning and deposition
5. Evaluation Re 1. Reacting the Mixed Alcoholate [0.8 $KO(C_2H_5)$/0.2 $NaO(C_2H_5)$] with TEA

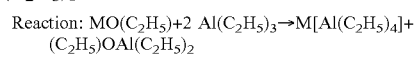

Reaction: $MO(C_2H_5)+2\ Al(C_2H_5)_3 \rightarrow M[Al(C_2H_5)_4]+(C_2H_5)OAl(C_2H_5)_2$ Source of Substances:
TEA from WITCOcrompton, Bergkamen (Germany); toluene distilled over $Na[Al(C_2H_5)_4]$;
$MO(C_2H_5)$ from own production.
Equipment: 500 ml 3-necked flask, precision glass stirrer, metering funnel, reflux condenser with indirect gasoline cooling, argon passage, silicone oil cooling bath.

Batch:

| | | |
|---|---|---|
| 29.9 g of $MO(C_2H_5)$ (m.w. 80.88) ≙ | 294.8 | mmol $KO(C_2H_5)$ |
| ≙ | 75.9 | mmol $NaO(C_2H_5)$ |
| Σ ≙ | 370.7 | mmol |
| 107 ml TEA = 88.8 g ≙ | 779.0 | mmol |
| 120 ml toluene | | |

Procedure:
The alcoholate was weighed into the reaction flask and suspended with 100 ml of toluene. The TEA weighed into a Schlenk vessel was placed in the metering funnel, and the vessel was washed with 20 ml of toluene. The TEA was added dropwise within 4 hours to the alcoholate suspension with stirring.

Instantaneous and distinct reaction at the drop-impact spot. Marked heating. The temperature was maintained at a maximum of 25° C. using an oil cooling bath. After addition of about 10% of the TEA amount, the suspension turned yellow at the drop-impact spot only, then the whole suspension turned yellow and gradually deep-orange thereafter.

After a total addition of about 50% of the TEA amount, abrupt decoloration occurred. The suspension, having returned to white, turned clear during further addition by dropping. After complete TEA addition, a clear, colorless solution was obtained. Final weight: 208.1 g.

Re 2. Removing the $Et_2AlOEt$ by-Component

The resulting reaction solution was transferred into a 500 ml 2-necked flask, and the toluene was subsequently condensed off under vacuum (0.1 mm) up to a bath temperature of 40° C.

91.9 g of toluene condensate, 116.2 g of liquid residue (theoretical amount: 118.7 g).

Two liquid phases were present after cooling to room temperature. The upper phase (smaller amount) was $Et_2AlOEt$.

The lower phase had largely crystallized overnight. Thus, there is a simple way of phase separation. In the present case, a route of separation by distillation was chosen.

All volatiles were distilled off in a high vacuum ($<1 \cdot 10^{-3}$ mm) up to a maximum bath temperature of 100° C.

45.2 g of distilled product=347.7 mmol $Et_2AlOEt$, i.e., 93.8% of theoretical amount
68.1 g of liquid residue=381 mmol $M[AlEt_4]$
$M[AlEt_4]_{(0.8\ K/0.2Na)}$, m.w.=178.8
Theoretical amount: 66.1 g.
The residue remains liquid even after several hours at 22° C.

Re 3. Adjusting the Final Mixture with TEA and Toluene
Addition of toluene and TEA.
Source of substances: TEA and toluene as described above.
Equipment: 500 ml 2-necked flask, metering funnel, stirring by means of 3 cm magnet in glass jacket, protective pot, argon passage.
Batch: 130 ml of toluene=112.3 g=1221.0 mmol, 51 ml TEA=42.3 g=371.3 mmol Procedure: the distillation residue was added with 110 ml of toluene at 22° C. with stirring, followed by dropwise addition of TEA and subsequently the remainder of toluene (washing of the metering funnel), likewise with stirring.

A clear, colorless solution was obtained. 213.8 g of electrolyte, $\kappa_{95° C.}$=15.6 mS/cm Re 4. Checking the Behavior Relating to Conditioning and Deposition To test the use as electrolyte in Al/Mg coating, conditioning and deposition were checked according to standard procedures. To this end, the deposition behavior was checked in several steps:
Anode material: alloy electrodes, AlMg 25.55×10×5 mm
Cathode: hexagonal screw 8.8 M 8×25
Cathode pretreatment: degreasing, descaling, ultrasound, $H_2O$ wash, vacuum drying, storage under argon
Cathode immersion depth: complete
Distance to anode: 10 mm, effective cathode surface: about 10 $cm^2$
Cathode movement: 60 rpm
Bath agitation: 2 cm magnet in glass jacket, 250 rpm
Temperature: 95–98° C.
Current density:
   01 1. Conditioning phase: 0.05 to 1.0 $A/dm^2$ (≙ 220 mAh)
   02 2. Conditioning phase: 1.0 to 2.0 $A/dm^2$ (≙ 140 mAh)
   03 3. Conditioning phase: 2.0 $A/dm^2$ (≙ 157 mAh)
   04 4. Deposition: 2.0 $A/dm^2$ (≙ 160 mAh)
   05 5. Deposition: 5.0 $A/dm^2$ (≙ 100 mAh)
Coating thickness: see description, current yield: not determined, final weight of coating: see description

DEPOSITIONS:

| | Final weight [mg] | Coating thickness calc. [μm] | Remarks |
|---|---|---|---|
| −01 | 64.7 | 27 | uniform, bright, dull, low spreading |
| −02 | 42.1 | 17 | uniform, silky gloss, improved spreading |
| −03 | 49.0 | 20 | partially dull, silky gloss, improved spreading |
| −04 | 41.2 | 16 | very good, glossy, normal spreading |
| −05 | 31.0 | 12 | coating good, somewhat duller than −04 |

In conditioning phase 1, the coating is bright, dull, being deposited with low spreading. The current density should not exceed 1.0 $A/dm^2$ in this case.

The magnesium concentration in the electrolyte increases with time, the deposition behavior is improved, spreading increases significantly, the coatings appear more silvery, and the current density resistance increases considerably. A cathodic current density of from 2.0 to 3.0 $A/dm^2$ is recommendable. The maximum load performed was 5 $A/dm^2$, but is certainly above this value when regarding the current density limit.

What is claimed is:

1. A method for the production of organoaluminum complex compounds of general formula $MAIR_4$ and mixtures of such compounds, wherein M represents Li, Na, K, Rb, Cs, $NR_4^+$, and R represents $CH_3$, $C_2H_5$, n- and/or iso-$C_3H_7$, n- and/or iso-$C_4H_9$, said method comprising reacting an alkanolate of general formula M(OR) in aromatic solvents, with at least one trialkylaluminum compound of general formula $AIR_3$ thereby producing organoaluminum complex compounds, and isolating the organoaluminum complex compounds from the reaction mixture, wherein the reaction is performed at temperatures of 25° C. at maximum.

2. The method according to claim 1, wherein the reacting is performed at temperatures of 20° C. at maximum.

3. The method according to claim 1, wherein said mixture of organoaluminum complex compounds is a mixture of $M^1AIR_4$ and $M^2AIR_4$, wherein $M^1$ and $M^2$ have the meaning of M and $M^1 \neq M^2$, and wherein the molar ratio of the $M^1AIR_4$ and $M^2AIR_4$ alkanolates is between 0.1 and 10.

4. The method according to claim 3, wherein $M^1$=K and $M^2$=Na, and the molar ratio of $M^1/M^2$ is 4:1.

5. The method according to claim 1, wherein R is an ethyl residue.

6. A method for the production of electrolyte solutions consisting of trialkylaluminum $AIR_3$, $M^1AIR_4$, $M^2AIR_4$ and an aromatic hydrocarbon in predetermined quantitative proportions, said method comprising producing a mixture $M^1AIR_4/M^2AIR4$ accoding to claim 3, and adding the aromatic hydrocarbon and $AIR_3$ in accordance with said predetermined quantitative proportions.

* * * * *